United States Patent [19]

Bredeweg et al.

[11] 4,234,541
[45] Nov. 18, 1980

[54] COMBUSTION CHAMBER CLEANING APPARATUS

[75] Inventors: Roger L. Bredeweg; George J. Sitek, both of Stevensville, Mich.

[73] Assignee: Leco Corporation, St. Joseph, Mich.

[21] Appl. No.: 16,975

[22] Filed: Mar. 2, 1979

[51] Int. Cl.³ .................. G01N 31/12; B01D 41/04; B08B 1/04; F23J 3/00

[52] U.S. Cl. .................. 422/78; 15/104.1 R; 15/104.2; 23/230 PC; 55/293; 134/166 C; 422/80

[58] Field of Search .............. 422/78, 207, 80; 23/230 PC; 110/119 R; 431/122; 196/122; 202/241, 263; 55/296, 293, 302; 134/22 C, 166–168 C; 15/104.1 R, 93 B, 104.1 C, 104.2, 68, 71

[56] References Cited

U.S. PATENT DOCUMENTS

| | | | |
|---|---|---|---|
| 1,824,994 | 9/1931 | Herold et al. | 15/68 |
| 2,022,985 | 12/1935 | Snow et al. | 196/122 |
| 2,248,903 | 7/1941 | Florez | 196/122 X |
| 3,608,278 | 9/1971 | Greenspan | 110/119 X |
| 3,668,833 | 6/1972 | Cahill | 110/119 X |
| 3,778,982 | 12/1973 | Birke | 55/293 |
| 3,836,434 | 9/1974 | Novy | 202/241 X |
| 4,091,747 | 5/1978 | Chase | 110/119 X |
| 4,115,072 | 9/1978 | Nielsen | 422/207 |

Primary Examiner—Michael S. Marcus
Attorney, Agent, or Firm—Price, Heneveld, Huizenga & Cooper

[57] ABSTRACT

For use in a combustion furnace for analytical apparatus in which a specimen is combusted in a combustion chamber and gases therefrom are withdrawn for analysis, a cleaning apparatus mounted at one end of the combustion chamber. The cleaning apparatus includes a housing sealably mounted to the combustion chamber and containing a movable cleaning element for abrading the interior walls of the combustion chamber. A shield is positioned between the cleaning element and the combustion chamber such that during combustion of a specimen, the cleaning element is effectively shielded from the high temperature combustion. In one embodiment, the housing also includes a filter between gas supply and exhaust passages and apparatus for self-cleaning of the filter.

14 Claims, 2 Drawing Figures

COMBUSTION CHAMBER CLEANING APPARATUS

BACKGROUND OF THE INVENTION

The present invention relates to combustion systems for analytical instruments and particularly to a system for cleaning the interior surface of a combustion chamber used therewith.

In combustion systems such as disclosed in U. S. Pat. No. 3,923,464, issued Dec. 2, 1975, to Sitek, et al., and assigned to the present assignee, a quartz tube is employed as a combustion chamber. A specimen in a crucible is positioned within the tube and heated by an induction coil for combusting the specimen. The gases emitted therefrom are subsequently analyzed For determining one or more constituent elements of the specimen. The combustion tube so used is capable of many cycles of operation; however, after each combustion, oxides and other contaminants typically expelled during the combustion process tend to coat the interior of the tube and can, if not removed, interfere with the accuracy of subsequent analyses.

In the past, the combustion tubes have been manually cleaned by an operator brushing them manually with a wire brush. This operation is not only time consuming and tedious but also subjects the combustion tube to breakage during handling and cleaning.

Combustion apparatus of the type described in the above identified patent ans systems such as Model No. CS-46, commercially available from Leco Corporation of St. Joseph, MI, include a filter in the gas flowpath between the source of oxidizing and carrier gas, such as oxygen, and the analyzer for removing particulate material from the combustion gases from a specimen. In the prior art systems above noted, it has been necessary to either replace the filter media or manually remove and clean the screen of the filter. This requirement, together with the requirement of manually cleaning the combustion tube, also leads to additional work for the operator and inconvenience as well as down time of the analyzer.

SUMMARY OF THE PRESENT INVENTION

The system of the present invention overcomes the problems encountered in the prior art by providing a cleaning system integrally constructed with the analyzer and coupled to one end of the combustion chamber for providing a longitudinally moveable cleaning member which can be rotated and extended along a significant portion of the length of a combustion chamber cleaning the interior walls thereof. According to another embodiment of the present invention, a dust filter is incorporated in a housing for the cleaning mechanism and is self-cleaning by providing a momentary gas pressure differential to remove particulate materials from the walls of the filter media.

Apparatus embodying the present invention include a combustion furnace having a combustion chamber with at least one open end and cleaning mechanism positioned in sealed relationship to at least one end of the combustion chamber. A cleaning member is longitudinally movable from a first position in the mechanism retracted from the combustion chamber to positions remote from the first position within the combustion chamber for cleaning the interior surface of the combustion chamber. According to one embodiment of the present invention, a housing is provided for the cleaning mechanism and includes a filter media integral therewith and extending in the gas flowpath from a source of oxidizing gas to an analyzer for collecting particulate by-products of combustion of a specimen. Means are provided for cleaning such filter while in place in the housing and collecting the removed particulate material.

It is an object of the present invention to provide a combustion furnace integrally including a cleaning mechanism for cleaning the interior surfaces of a combustion chamber associated therewith and/or a filter in the gas flowpath.

A feature of the present invention is the provision of a housing positioned in sealed engagement with one end of a combustion chamber and including therein a cleaning element extendable from the housing into the combustion chamber for cleaning the interior walls thereof. According to another feature of the present invention, the housing also includes a filter in the gas flowpath from a source of gas into the combustion chamber and to an analyzer associated with the combustion furnace. According to another feature of the present invention, the cleaning element is shielded from the combustion chamber.

This construction advantageously provides a combustion chamber cleaning mechanism integral with the combustion furnace as well as a filter media which can be cleaned in place.

These and other objects, features, and advantages of the present invention can best be understood by reference to the following description thereof, together with the drawings in which:

DETAILED DESCRIPTION OF THE PREFERRED EMBODIMENT

Figure 1:
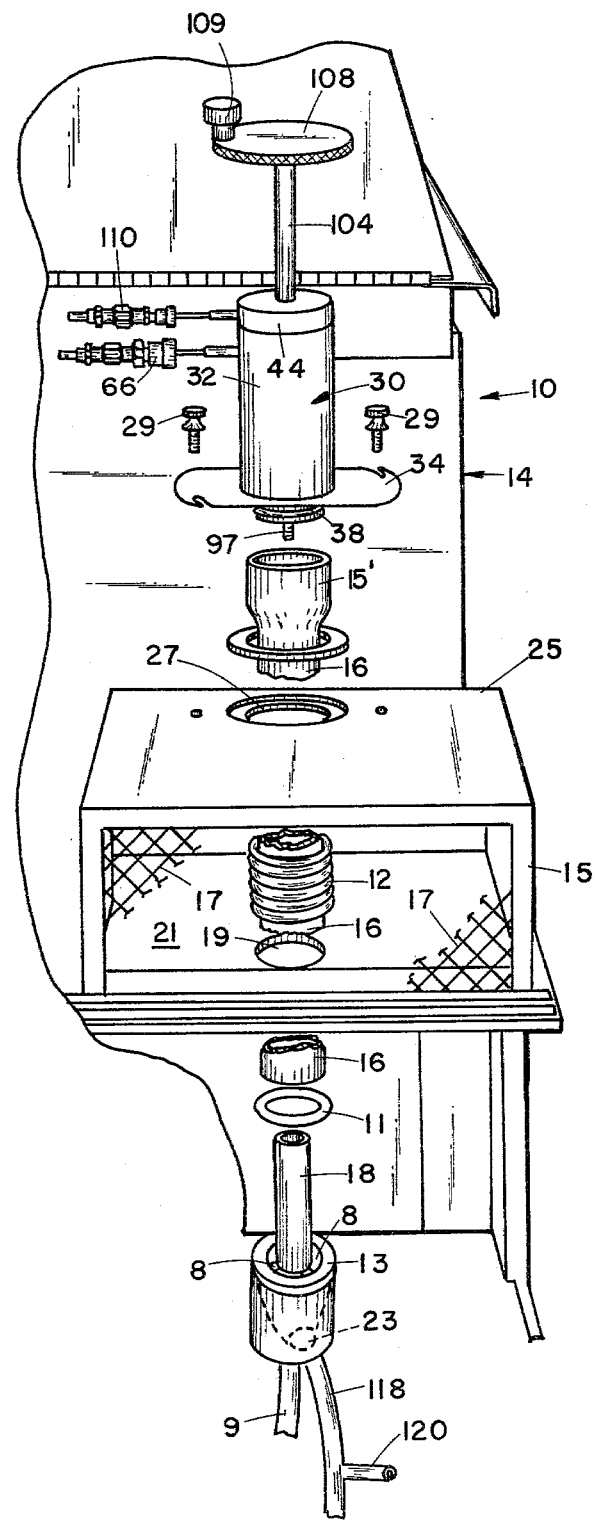
FIG. 1 is an exploded fragmentary perspective view of a combustion furnace including the apparatus of the present invention.

Referring initially to FIG. 1, there is shown a combustion furnace 10 including an induction coil 12 activated by a source of RF energy contained within the furnace housing 14. The induction coil surrounds a quartz combustion tube 16 in concentric relationship for heating of a specimen such as a steel, 1 gram, or the like sample for analysis. The sample is positioned within a ceramic crucible of the type disclosed in U. S. Pat. No. 3,100,155, issued Aug. 6, 1963, to H. C. Wagner, and assigned to the present assignee, or its equivalent. The crucible is positioned within the center of the longitudinally extending cylindrical combustion tube 16 by means of a vertically movable cylindrical pedestal 18 mounted to the furnace and movable upwardly to position the crucible within the approximate center of the induction coil 12.

A cup-shaped sealing element 13 supports pedestal 18 and a seal 11 is positioned over the end of tube 16 and sealably engages the cup 13 and floor 21 when the pedestal 18 is in the raised position. A cup 13 is vertically moved by a piston rod 9 coupled to a cylinder, A particle removal conduit 118 extends into the funnel-shaped interior of cup 13 adjacent rod 9 and has an open end 23 communicating with the interior of the combustion tube through slots 8 for providing oxygen to the combustion chamber and for removal of particulate material from the chamber as described below.

The furnace shown in FIG. 1 includes a cage 15 surrounding the combustion tube and induction coil and including a mesh face 17 permitting visual inspection of the combustion chamber during operation but providing RF shielding. The cage has a ceiling 25 with an aperture 27 for the tube 16 and a floor 21 with an aperture for the tube.

A specimen positioned within the crucible is heated by the induction coil to temperatures of approximately 1700° F. to burn the specimen in an oxygen atmosphere to provide therefrom a gaseous specimen for analysis. Thus, the system can be used, for example, to analyze the carbon and sulphur content of a steel specimen and in such case, the carbon element is converted to carbon monoxide and carbon dioxide while the sulphur is converted to sulphur dioxide which is subsequently applied to an analyzer 20 (FIG. 2) for detection of the quantity of the constituent gaseous elements.

Figure 2:
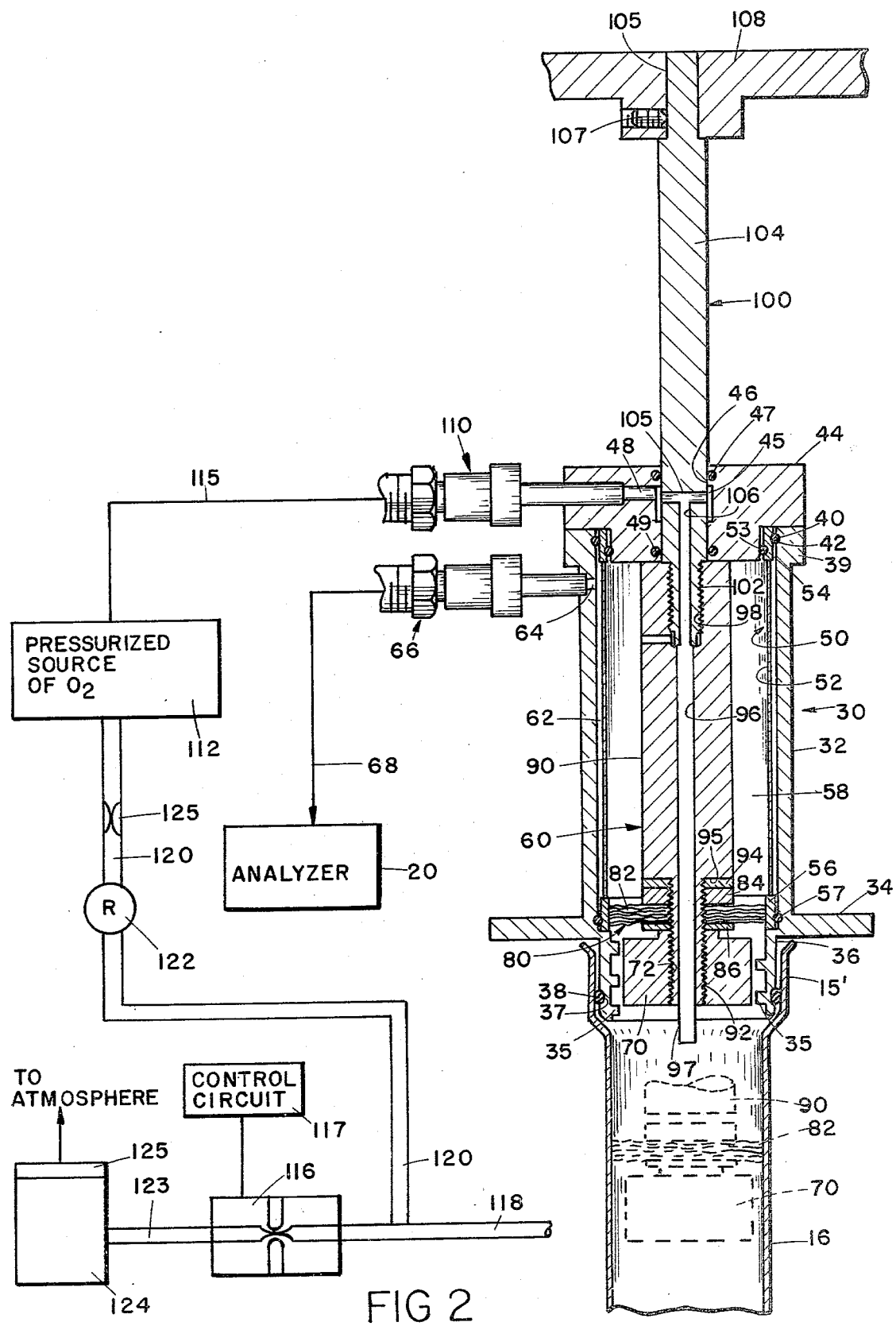
FIG. 2 is an enlarged fragmentary vertical cross-sectional view of the apparatus of the present invention shown in FIG. 1.

Sealably mounted above the combustion chamber comprising tube 16 in the preferred embodiment is the cleaning and filter mechanism 30 of the present invention which is now described in detail in conjunction with FIG. 2.

As seen in FIG. 2, the combustion chamber comprising a quartz tube 16 has an enlarged bell-shaped upper end 15' for receiving the lower end of the cleaning filter mechanism 30. The cleaning mechanism 30 comprises a cylindrical housing 32 having a horizontally and outwardly extending mounting flange 34 near the lower or first end and a cylindrical projection 36 extending below flange 34 and including an annular recess 37 on the outer surface near the end for receiving an O-ring seal 38. The outer diameter of cylindrical projection 36 is such that it is somewhat smaller than the internal diameter of the bell-shaped end 15' of combustion chamber 16 such that it extends therein as shown in FIG. 2 with the O-ring 38 sealably enclosing the upper end of the combustion chamber to the housing 32. The elongated cylindrical housing 32 terminates at an upper end in a second flange 39 including an inner annular recess 40 for receiving therein an O-ring 42.

A cover plate 44 having a longitudinally extending axially aligned aperture 46 is positioned to enclose the upper or second end of the housing 32 through an annular collar 54 of an elongated cylindrical filter member 50. Filter 50 is shaped in the form of a cylinder and comprises a two layered screen having a coarse outer layer comprising a 30×30 mesh screen for supporting a fine five micron mesh inner screen (i.e., facing the longitudinal axes of the housing 32). Both of the screens are made of stainless steel to resist wear and erosion. The screens 52 are secured at opposite ends by an upper collar 54 and a lower collar 56. Upper collar 54 includes a pair of longitudinally spaced annular recesses on opposite sides for receiving O-rings 53 and 42, respectively, for sealably enclosing the cover plate 44 to the upper end of the housing 32. The lower collar 56 likewise includes an annular recess for receiving an O-ring 57 sealably mounting the filter to the internal cylindrical wall of housing 32. Filter 50 is coaxially positioned within housing 32 to define an inner chamber 58 and an outer annular chamber 62.

Formed on the cylindrical extension 36 of housing 32 along the interior cylindrical surface thereof is a spiral thread 35 of square cross section and having a pitch of four threads per inch. Thread 35 defines a spiral path for swirling combustion gases around the internal diameter of the lower end of housing 32 for protecting the cleaning mechanism as described in greater detail below.

The housing 32 for the cleaning apparatus is secured to the ceiling 25 of furnace 14 by flange 34 and secured by means of screws 29 to securely position the housing with its lower end sealably mounted within the upper end of the combustion chamber 16.

Within the housing 32 there is provided a movable cleaning assembly 60 including a shield element 70, a cleaning element 80, a spacer 90, and drive means 100 for moving the cleaning element. The spacer element 90 comprises a cylindrical rod having a threaded stud 92 at its lower end onto which there is first positioned a lock washer 94 and subsequently the cleaning element 80. Cleaning element 80 comprises a stainless steel circular wire brush 82. The diameter of wire brush 82 is slightly greater than the internal diameter of combustion tube 16 for abrading the interior surface of the combustion tube as described below. Brush 82 is integrally mounted between upper and lower disc supports 84 and 86, respectively, in a permanent fashion and securely held against the annular shoulder 95 of spacer 90 and lock washer 94 by means of the circular plug shield 70. The brush is, thus, mounted to shaft means constituting, in part, the spacer 90 and drive means 100.

Shield 70 includes an internally threaded aperture 72 corresponding to the thread 92 of the threaded projection on spacer 90. Shield or plug 70 has a diameter to provide about 0.005 inches clearance with respect to the end of thread 35 and a longitudinal length substantially the same as the longitudinal length of thread 35. With the brush 82 in the first or retracted position shown in solid lines in FIG. 2, plug 70 aligns with thread 35 to define shield means for the brush 82.

Spacer 90 includes an axially extending aperture 96 extending the length of the spacer and includes a lance tube 97 extending downwardly from the end of projection 92. Lance 97 is a ⅛ inch outer diameter stainless steel tube force fitted within aperture 96 for directing oxygen into the open mouth of a crucible (not shown) to assist in combustion as it is well known in the art. The upper end of spacer 90 includes a female threaded aperture 98 for receiving a male threaded projection 102 associated with the drive means 100 comprising in part a shaft 104. Shaft 104 includes an axially extending aperture 106 extending from the end of threaded projection 102 upwardly to communicate with a radially extending aperture 105 extending through the cylindrical rod. Plug 44 includes an annular recess 45 axially aligned with aperture 105 to define a manifold sealed at its upper end by an O-ring seal 47 fitted within a channel formed in the inner cylindrical wall of cylindrical aperture 46 through cap 44 and a lower O-ring seal 49 similarly mounted on the opposite side of manifold 45. This mounting arrangement provides a sliding seal between shaft 104 and the cap 44 permitting the shaft to rotate and move longitudinally. At the upper end of shaft 104 there is mounted a handle 108 secured to a reduced diameter portion 105 of the shaft by means of a set screw 107. Handle 108 can, as described below, be manually rotated by means of a knob 109 (FIG. 1) for rotating the shaft and cleaning element mounted thereto.

Extending radially inwardly from the outer edge of cover plate or cap 44 is an aperture 48 communicating with manifold 45 and into which there is provided a gas fitting 110 coupled to a source of pressurized oxygen 112 by means of a conduit 115. Oxygen from source 112 is also applied to conduit 118 by means of a conduit 120 which includes in series therewith a pressure regulator 122 set for 11 psi and a flow restriction orifice 125. Conduit 120 is coupled to conduit 118 by means of a conventional T-fitting with the leg of the T extending away from the combustion chamber end 23 of conduit 118 coupled to a pneumatically actuated pinch valve 116 having its outlet coupled by means of a conduit 123 to a dust collecting chamber 124. As will be described in greater detail below, the monentary actuation of valve 116 by a circuit 117 greatly reduces the internal pressure of the combustion chamber causing a reverse gas flowpath through conduit 118, valve 116, and conduit 123 into the chamber 124 which is vented to the atmosphere through a dust filter 125. This removes particulate material from the combustion chamber and chamber 58 into the collection chamber 124.

Oxygen from source 112 is applied by aperture 48 to lance 97 by manifold 45 and apertures 105, 106, and 96. The combustion gases, in turn, enter chamber 58 through brush 82 and thread 35 and pass through filter 50 to an outer chamber 62. Communicating with the outer annular chamber 62 is an axially entending outlet passage 64 coupled to a gas fitting 66, in turn coupled to analyzer 20 by means of conduit 68.

OPERATION

In use, the combustion system and analyzer of the present invention is cycled through several analyses of specimens in a manner generally similar to that set forth in U. S. Pat. No. 3,985,505, issued Oct. 12, 1976, to Bredeweg, assigned to the present assignee, the disclosure of which is incorporated herein by reference. Basically, the specimen and perhaps an accelerator is positioned in a ceramic crucible mounted on pedestal 18 and raised into the combustion chamber comprising the combustion tube 16. The induction coil 12 is then activated as is the gas supply to provide a flow of oxygen from lance 97 into the mouth of the combustion tube as the specimen is heated to a temperature sufficient to complete the combustion of the specimen to its constituent gases. The gas flowpath is from lance 97 into the combustion tube and thence upwardly in a spiral path around the helical thread 35 thereby elongating and greatly cooling the gas before it reaches the area of brush 82. The brush is naturally permeable to the combustion gases allowing them to pass upwardly into inner chamber 58 between the outer wall of spacer 90 and screen 52 of filter 50. The gas then passes through the filter into chamber 62 and thence outwardly through the axial outlet 64 to analyzers 20 through conduit 68.

After several cycles of analysis, the interior cylindrical surface of the combustion chamber 16 becomes coated with oxides such as tin, iron, and tungsten, as well as metallic elements which may splash from the crucible onto the combustion chamber wall. In order to remove such material, the cleaning mechanism of the present invention is employed by rotating handle 108 by knob 109 and pressing downwardly which permits the wire brush 82 to thread its way through the helical thread 35 while the sliding fit between shaft 104 and aperture 46 permits the shaft 104 to extend within the cylindrical housing 32 as the brush enters the combustion tube in a cleaning position as shown in phantom form in FIG. 2. To effectively clean the interior of the tube as the handle is pushed downwardly into the tube, it is continually rotated such that the ends of the wires forming the stainless steel wire brush 82 scrape the combustion tube wall. The mechanism is then returned to its first position shown in solid lines in FIG. 2. Naturally, shaft 104 is selected to be sufficiently long such that brush 82 can reach substantially the length of the combustion tube. The material removed drops to the bottom of the tube where it can easily be removed by lowering pedestal 18 opening the bottom of the tube.

It also is desired to frequently clean the filter 50 which can be done with the filter in place by actuating pop value 116 momentarily. During normal operation, the interior of chamber 58 is maintained at approximately 11 psi pressure. With the cleaning mechanism in its first position, valve 116 can be momentarily actuated by a control circuit 117 to vent the combustion chamber to the chamber 124 for a few milliseconds thus greatly reducing the pressure in chamber 58 momentarily. This flexes the filter screen 52 and causes a gas flow from chamber 62 to chamber 58 causing the particulate material collected on the interior cylindrical wall of the filter to drop into the bottom of housing 32. The collected material is fine and will easily fall through the wire brush to the fullen-shaped floor of cap 13 into opening 23 for removal within the ⅜ inch conduit 118 and into the collection chamber 124 through conduit 123 and valve 116.

Thus, applicants' system provides a cleaning mechanism for a combustion chamber which is sealably mounted to one open end of the chamber and includes shield means protecting the cleaning mechanism during a cycle of combustion by providing, in part, an elongated flowpath for gases from the combustion chamber into an integral cleaning mechanism housing and filter chamber. Means are provided for moving the cleaning mechanism from a position external to the combustion chamber to within the combustion chamber for removing material from the walls of the combustion chamber. Further, applicants' system provides means including a commercially available pinch valve 116 for back flushing a cylindrical filter media contained within the integral cleaning mechanism housing and filter chamber and a collection chamber for material so removed.

It will become apparent to those skilled in the art that the manually operated cleaning mechanism employing handle 108 could be replaced with a rotatable and advancing drive of a suitable nature such as a motorized screw thread or the like to achieve the cleaning of chamber 16 automatically.

These and other variations and modifications to the preferred embodiment of the invention described herein, however, will become apparent to those skilled in the art and can be made without departing from the spirit or scope of the invention as defined by the appended claims.

The embodiments of the invention in which an exclusive property or privilege is claimed are defined as follows.

1. For use with a combustion chamber for combusting solid or liquid specimens for subsequent analysis of gases therefrom, a cleaning system for cleaning the combustion chamber comprising:
   a cylindrical housing for rotatably and slideably supporting a cleaning brush;
   a cleaning brush rotatably and slideably supported by said housing and including shaft means for moving said brush between a retracted position within said housing and from an end of said housing to operative cleaning positions extended from said housing, a plug mounted to said shaft adjacent said brush on a side of said brush adjacent said end of said housing when said brush is retracted within said housing; and said end of said housing including internal thread means extending inwardly and aligned with and radially spaced from said plug when said brush is in a retracted position within said housing to form a spiral pathway for gas exiting from a combustion chamber.

2. A combustion chamber for combusting solid or liquid specimens for subsequent analysis of gases therefrom and a cleaning system for cleaning the combustion chamber comprising:

means defining a cylindrical combustion chamber having an open end;

a housing for movably supporting a cleaning element wherein one end of said housing is shaped to fit within said open end of said combustion chamber, and seal means extending around said one end of said housing to seal the junction of said one end of said housing and said combustion chamber;

a cleaning element comprising a shaft and means for mounting a generally circular brush to said shaft, said housing including means for mounting said shaft for rotational and longitudinal movement with respect to said housing between a first position within said housing and operative positions within the combustion chamber; and shield means comprising a spiral thread extending radially inwardly from an interior wall of said one end of said housing, said thread positioned below said brush when said brush is in said first position, and a circular plug mounted to said shaft to align with said thread when said brush is in said first position, said plug having a diameter to provide a slight clearance between said thread and the outer cylindrical wall of said plug and a length extending substantially the longitudinal length of said thread thereby forcing combustion gases to swirl around said thread before reaching said brush.

3. The apparatus as defined in claim 2 wherein said brush is a wire brush

4. The apparatus as defined in claim 3 and further including filter means positioned in said housing to divide said housing into first and second chambers and gas inlet means communicating with said first chamber and gas outlet means communicating with said second chamber.

5. A system for cleaning the interior wall of a cylindrical combustion chamber used for combusting samples for analysis comprising:

means defining a cylindrical combustion chamber, a generally cylindrical housing including means for sealably mounting one end of said housing to an open end of said combustion chamber; to enclose the open end of said combustion chamber:

a cleaning brush supported within said housing for rotational and longitudinal motion from a first position in the housing to a cleaning position within the combustion chamber in which said brush can be rotated to engage the interior of said combustion chamber to clean said combustion chamber, means for moving said cleaning brush between said first and cleaning positions; and shield means cooperating with said one end of said housing and said cleaning brush to shield said cleaning brush from said combustion chamber in said first position.

6. A system for cleaning the interior wall of a cylindrical combustion chamber used for combustion samples for analysis comprising:

means defining a cylindrical combustion chamber having an open end, a generally cylindrical housing including means for sealably mounting one end of said housing including means for sealably mounting one end of said housing to said open end of said combustion chamber to enclose said open end of said combustion chamber;

a cleaning brush supported within said housing for rotational and longitudinal motion from a first position in the housing to a cleaning position within said combustion chamber;

means for moving said cleaning element between said first and cleaning positions; and shield means positioned between said cleaning brush and said combustion chamber to shield said cleaning element, wherein said shield means comprises a spiral thread extending radially inwardly from an interior wall of said one end of said housing, said thread positioned below said brush when said brush is in said first position, and a circular plug mounted to said shaft to align with said thread when said brush is in said first position, said plug having a diameter to provide a slight clearance between said thread and the outer cylindrical wall of said plug and a length extending substantially the longitudinal length of said thread thereby forcing combustion gases to swirl around said thread before reaching said brush.

7. The apparatus as defined in claim 6 wherein said cleaning element comprises a shaft and means for mounting a generally circular brush to said shaft, said housing including means for mounting said shaft for rotation and longitudinal movement with respect to said housing between said first position within said housing and said operative positions within the combustion chamber.

8. The apparatus as defined in claim 7 wherein said brush is a wire brush.

9. The apparatus as defined in claims 5 or 8 and further including a cylindrical filter coaxially supported within said housing in spaced relationship to the interior wall of said housing and sealed at opposite ends to the wall of said housing to define an inner chamber and an outer chamber separated by said filter, said housing including means for supplying a carrier gas to the combustion chamber and for receiving by-product gases of combustion in said inner chamber, said housing further including gas outlet means communicating with said outer chamber, and means for rapidly changing the gas pressure within said housing for flexing said filter to remove captured particles therefrom.

10. The apparatus as defined in claim 9 and further including a particulate removal conduit mounted with an open end communicating with the combustion chamber and coupled to said means for changing the pressure for providing a conduit for the flow of particulate material from the combustion chamber.

11. The apparatus as defined in claim 10 and further including a particulate collection chamber coupled to said particulate removal conduit for collecting particulate material.

12. A combustion furnace for combusting a specimen for analysis and filter means comprising:
- a cylindrical combustion chamber having an open end;
- a cylindrical housing including means for sealably mounting one end of said housing to said open end of said combustion chamber and means enclosing the remaining end of said housing;
- a cylindrical filter coaxially supported within said housing in spaced relationship to the interior walls of said housing and sealed at opposite ends to the wall of said housing to define an inner chamber and an outer chamber separated by said filter;
- said housing including means for supplying a carrier gas to said combustion chamber and for receiving gases of combustion from said combustion chamber in said inner chamber;
- said housing further including gas outlet means communicating with said outer chamber; and
- means for rapidly changing the gas pressure within said housing comprising means defining a source of pressurized gas coupled to said inner chamber and momentarily actuated valve means for momentarily venting said inner chamber to a lower pressure thereby rapidly decreasing the pressure in said inner chamber, flexing said cylindrical filter for removing captured particles from said filter.

13. The apparatus as defined in claim 12 and further including a particulate collection chamber coupled to said combustion chamber for collecting particulate material removed by the pressure change.

14. The apparatus as defined in claim 13 and further including a cleaning element mounted within said housing for selective movement into said combustion chamber for cleaning the interior wall of the combustion chamber.

* * * * *

UNITED STATES PATENT AND TRADEMARK OFFICE
CERTIFICATE OF CORRECTION

PATENT NO. : 4,234,541                                         Page 1 of 2

DATED : November 18, 1980

INVENTOR(S) : Roger L. Bredewig, et al

It is certified that error appears in the above—identified patent and that said Letters Patent is hereby corrected as shown below:

Column 1, line 16:

"For" should be --for--

Column 1, line 30

"ans" should be --and--

Column 1, line 49

"moveable" should be --movable--

Column 5, line 11

"monentary" should be --momentary--

Column 5, line 4

(bold print) "11" should be --(normal print) 11--

UNITED STATES PATENT AND TRADEMARK OFFICE
CERTIFICATE OF CORRECTION

PATENT NO. : 4,234,541

DATED : November 18, 1980

INVENTOR(S) : Roger L. Bredewig, et al

It is certified that error appears in the above—identified patent and that said Letters Patent is hereby corrected as shown below:

Column 7, line 44

"brush" should be --brush.--

Column 8, lines 9 and 10

"housing including means for sealably mounting one end of said" should be --deleted--

Signed and Sealed this

Eighteenth Day of August 1981

[SEAL]

Attest:

Attesting Officer

GERALD J. MOSSINGHOFF

Commissioner of Patents and Trademarks